United States Patent [19]

Fabry et al.

[11] Patent Number: 5,072,015

[45] Date of Patent: Dec. 10, 1991

[54] CARBONIC ACID FATTY ALCOHOL ESTER SULFONATES, A PROCESS FOR THEIR PRODUCTION AND SURFACE-ACTIVE AGENTS CONTAINING THEM

[75] Inventors: Bernd Fabry, Korschenbroich; Alfred Westfechtel; Horst Eierdanz, both of Hilden; Ansgar Behler, Bottrop, all of Fed. Rep. of Germany

[73] Assignee: Henkel Kommanditgesellschaft auf Aktien, Duesseldorf-Holthausen, Fed. Rep. of Germany

[21] Appl. No.: 383,104

[22] Filed: Jul. 20, 1989

[30] Foreign Application Priority Data

Jul. 20, 1988 [DE]  Fed. Rep. of Germany ....... 3824720

[51] Int. Cl.$^5$ .............................................. C07C 69/96
[52] U.S. Cl. ..................................... 558/276; 558/51
[58] Field of Search .................................. 558/51, 276

[56] References Cited

U.S. PATENT DOCUMENTS 4,545,939 10/1985 Sekiguchi et al. ................. 260/400
4,792,419 12/1988 Piorr et al. .......................... 562/110
4,826,998  5/1989 Veitenhansl et al. ................ 549/14

FOREIGN PATENT DOCUMENTS 60-186599  9/1985  Japan .

OTHER PUBLICATIONS

J. Chem. Soc. 117, p. 708, 1920.
Chemische Berichte, 1981, T. Grieser, p. 210.

Methoden Der Organischen Chemie, U. Petersen, pp. 66–68.
Surfactants in Consumer Products, London, J. Falbe, pp. 71–73 (1987).
J. Prakt. Chem., 22, Dr. Ludwig Schreiner, pp. 353–361 (1980).
Chemische Berichte, 1981, T. Grieser, pp. 1210–1215.

*Primary Examiner*—C. Warren Ivy
*Assistant Examiner*—Celia Chang
*Attorney, Agent, or Firm*—Ernest G. Szoke; Wayne C. Jaeschke; Real J. Grandmaison

[57] ABSTRACT

Carbonic acid fatty alcohol ester sulfonates prepared by sulfonation of carbonic acid fatty alcohol esters corresponding to formula I

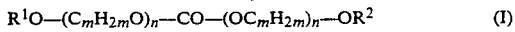
$$R^1O-(C_mH_{2m}O)_n-CO-(OC_mH_{2m})_n-OR^2 \qquad (I)$$

in which $R^1O$ is a residue of a fatty alcohol containing 16 to 22 carbon atoms and at least one olefinic double bond,
$R^2O$ is a residue of a saturated alkanol containing 1 to 22 carbon atoms or a residue of a fatty alcohol containing 16 to 22 carbon atoms and at least one olefinic double bond,
$m$ is a number 2 or 3 and
$n$ is a number of 0 to 20, and subsequent neutralization and hydrolysis of the sulfonation products with a base.

9 Claims, No Drawings

CARBONIC ACID FATTY ALCOHOL ESTER SULFONATES, A PROCESS FOR THEIR PRODUCTION AND SURFACE-ACTIVE AGENTS CONTAINING THEM

BACKGROUND OF THE INVENTION

1. Field of the Invention

This invention relates to carbonic acid fatty alcohol ester sulfonates prepared by sulfonation of carbonic acid fatty alcohol esters corresponding to formula I $$R^1O-(C_mH_{2m}O)_n-CO-(OC_mH_{2m})_n-OR^2 \quad (I)$$

in which $R^1O$ is a residue of a fatty alcohol containing 16 to 22 carbon atoms and at least one olefinic double bond, $R^2O$ is a residue of a saturated alkanol containing 1 to 22 carbon atoms or a residue of a fatty alcohol containing 16 to 22 carbon atoms and at least one olefinic double bond, m is the number 2 or 3 and n is a number of 0 to 20, and subsequent neutralization and hydrolysis of the sulfonation products with bases.

2. Discussion of Related Art

Sulfonates and lower alkyl esters of unsaturated carboxylic acids are surface-active compounds which may be prepared from lower alkyl esters of unsaturated fatty acids by reaction with sulfur trioxide and subsequent neutralization and hydrolysis, for example in accordance with European Patent Application 0,130,753. The structure of the sulfonates ultimately obtained has not yet been fully elucidated. It may be assumed that mixtures consisting, inter alia, of alkene and hydroxyalkane sulfonates are obtained, cf. J. Falbe, Surfactants in Consumer Products, pages 72-73, (1987), Springer-Verlag, Berlin.

DESCRIPTION OF THE INVENTION

Other than in the operating examples, or where otherwise indicated, all numbers expressing quantities of ingredients or reaction conditions used herein are to be understood as modified in all instances by the term "about."

It has now been found that carbonic acid fatty alcohol ester sulfonates, which are sulfonation products of the carbonic acid fatty alcohol esters corresponding to formula I above, are compounds having interesting surface-active properties which, surprisingly, are also almost completely stable to hydrolysis at pH values in the range from 0 to 13.

The starting products for the preparation of the compounds according to the invention, i.e. fatty acid esters of carbonic acid, are known and may be obtained by reaction of fatty alcohols with phosgene or chloroformic acid esters; cf. J. Chem. Soc. 117, 708 (1920), J. Prakt. Chem. 22, 353-360 (1880). An even simpler synthesis is based on the transesterification of fatty alcohols with diethyl carbonate in the presence of alkaline catalysts; cf. Chem. Ber. 114, 1210-1215 (1981), Houben-Weyl, Methoden der organischen Chemie, 4th Edition, Vol. E4, pages 66 et seq. Difatty alcohol esters or mixed fatty alcohol esters of carbonic acid may be similarly prepared by the last of the above-mentioned processes.

In general formula I, the group $R^1O$ is a residue of a fatty alcohol containing 16 to 22 carbon atoms and one or more olefinic double bonds, preferably 1 or 2 olefinic double bonds. Fatty alcohols such as these may be of synthetic and, in particular, natural origin. Typical representatives of suitable natural fatty alcohols containing 1 or 2 olefinic double bonds are oleyl, elaidyl, linoleyl, gadoleyl, arachidonic, erucic and brassidyl alcohol. As is standard practice in oleochemistry, these alcohols may be used in the form of their technical grade mixtures with other saturated or unsaturated fatty alcohols of the type obtainable from animal or vegetable oils and fats, for example palm oil, palm kernel oil, soybean oil, rapeseed oil, olive oil, sunflower oil and the like by hydrogenation of the fatty acid esters present therein.

Technical grade cetyl/oleyl cuts having iodine values in the range from 50 to 130 are particularly preferred for the purposes of the invention.

The group $R^2O$ may have the meaning defined above for $R^1O$. In addition, the group $R^2O$ may also be the residue of a saturated alkanol containing 1 to 22 carbon atoms. Typical representatives of such alkanols are methanol, ethanol, propanol, butanol, pentanol, hexanol, 2-ethyl hexanol, octanol, nonanol, decanol, dodecanol, tetradecanol, hexadecanol, eicosanol and docosanol. Particular preference is attributed to a residue $R^2O$ derived either from ethanol or from saturated fatty alcohols containing 16 to 18 carbon atoms, the saturated fatty alcohols being used in the form of their technical grade mixtures, containing predominantly these fatty alcohols, with other fatty alcohols, as is standard practice in oleochemistry.

In accordance with the meaning defined for m in formula I (m=2 or 3), the carbonic acid fatty alcohol esters may also be used in the form of esters of carbonic acid with adducts of ethylene oxide, propylene oxide or ethylene oxide and propylene oxide (with random or block distribution of the alkylene oxide units) with unsaturated fatty alcohols containing 16 to 22 carbon atoms or saturated alkanols containing 1 to 22 carbon atoms. Each of the groups $R^1O$ and $R^2O$ may be provided with 1 to 20 ethyleneoxy and/or propyleneoxy groups.

Carbonic acid fatty alcohol ester sulfonates obtainable by sulfonation of carbonic acid fatty alcohol esters corresponding to formula I, in which $R^1O$ is an oleyloxy group, $R^2O$ is an oleyloxy, cetyloxy, stearyloxy or ethyloxy group, m is the number 2 and n is a number of 0 to 10, are particularly preferred.

In this case, also, it is possible to use carbonic acid fatty alcohol esters in which the group $R^1O$ and, optionally, the group $R^2O$ are derived from technical grade fatty alcohol mixtures containing predominantly oleyl alcohol; similarly, it is again possible to use adducts of 1 to 10 mol ethylene oxide with the fatty alcohols or fatty alcohol mixtures mentioned.

Suitable sulfonating agents are any of those normally used for the sulfonation of olefins, including for example sulfuric acid, chlorosulfonic acid, oleum, amidosulfonic acid or sulfur trioxide; sulfur trioxide, particularly gaseous sulfur trioxide, being preferred.

The carbonic acid fatty alcohol esters of formula I used in accordance with the invention contain an olefinic double bond in the group $R^1O$ and, optionally, in the group $R^2O$; they are capable of reacting with at least 1 mol of sulfur trioxide per double bond in the preparation of the subject compounds. However, it is not necessary to sulfonate all the olefinic double bonds in the carbonic acid fatty alcohol esters used, so that it is also possible, for example, to obtain diesters of carbonic acid with unsaturated fatty alcohols sulfonated with, on average, 1 mol of sulfur trioxide.

The carbonic acid fatty alcohol esters corresponding to formula I may be sulfonated as known for fatty acid lower alkyl esters, for example with gaseous sulfur trioxide in suitable reactors, particularly of the falling film type. The sulfur trioxide is diluted with air or nitrogen and is preferably used in the form of a gas mixture containing approximately 1 to 8% by volume, and more especially 3 to 5% by volume of sulfur trioxide. The reaction is preferably carried out in the absence of solvents, although any of the solvents typically used for the sulfonation of unsaturated fatty acid esters, olefins, aromatics and the like may also be used.

The carbonic acid fatty alcohol ester sulfonates according to the invention are preferably prepared by sulfonation in a ratio of 0.5 to 1.8, preferably in a ratio of 0.6 to 1.5 and, more preferably, in a ratio of 1.0 to 1.3 mol of sulfur trioxide per mol of the olefinic double bonds present in the carbonic acid fatty alcohol esters corresponding to formula I at a temperature in the range from 15° to 80° C., and more especially at a temperature in the range from 40° to 60° C.

The sulfonation product obtained is then neutralized and hydrolyzed with a base, particularly an aqueous base, at a pH value of at least 6 to 13, and more especially at a pH value of 7 to 12. Suitable bases are alkali metal hydroxides, such as sodium, potassium and lithium hydroxide, alkaline earth metal oxides and hydroxides, such as magnesium oxide, magnesium hydroxide, calcium oxide and calcium hydroxide, ammonia and organic bases, such as ethanolamine, diethanolamine or triethanolamine and primary, secondary and tertiary alkylamines. Alkali metal and alkaline earth metal hydroxides and ammonia are preferably used in the form of more or less concentrated aqueous solutions. Alkali metal and alkaline earth alkoxides are also suitable for neutralization with anhydrous bases.

In another advantageous embodiment of the invention, the neutralized sulfonation products are hydrolyzed over a period of 15 to 240 minutes at a temperature of at least 70° C., the upper limit to the hydrolysis temperature being determined by the boiling point of the water. However, hydrolysis may also be carried out under pressure at temperatures above 100° C.

Where the carbonic acid fatty alcohol esters used contain proportions of esters of saturated fatty alcohols, as is entirely possible when they are produced from technical grade fatty acid cuts, these esters of saturated fatty alcohols may either remain in the carbonic acid fatty alcohol ester sulfonates according to the invention or, if desired, may be removed in known manner, for example by phase separation. Corresponding processes are known per se for sulfonates of lower alkyl esters of unsaturated fatty acids, cf. the above-cited European Patent Application 0,130,753.

In the preparation of the carbonic acid fatty alcohol ester sulfonates according to the invention by sulfonation of carbonic acid fatty alcohol esters corresponding to formula I, cyclic or bridged sulfonation products may be formed as intermediate stages, necessitating hydrolysis in the manner described above to avoid gradual reacidification of the products. The ester bonds present are surprisingly not hydrolyzed.

The present invention also relates to a process for the production of carbonic acid fatty alcohol ester sulfonates having the features mentioned above. The invention also relates to surface-active agents containing, individually or in admixture, carbonic acid fatty alcohol ester sulfonates corresponding to formula II $$R^3O\text{—}(C_mH_{2m}O)_n\text{—}CO\text{—}(OC_mH_{2m})_n\text{—}OR^4 \quad (II)$$

in which $R^3O$ is a residue corresponding to formula IIIa or IIIb $$CH_3\text{—}(CH_2)_x\text{—}CH(OH)\text{—}(CH_2)_y\text{—}CH(SO_3M\text{-})\text{—}(CH_2)_z\text{—}CH_2\text{—}O\text{—} \quad (IIIa)$$

or $$CH_3\text{—}(CH_2)_x\text{—}CH(SO_3M)\text{—}(CH_2)_y\text{—}CH(OH\text{-})\text{—}(CH_2)_z\text{—}CH_2\text{—}O \quad (IIIb)$$

in which x and z are a number of 0 to 18, y is the number 0, 1 or 2 and

M is an alkali metal, ammonium or, optionally, mono-, di- or trialkyl- or hydroxyalkyl-substituted ammonium ion, the sum of $x+y+z$ being a number in the range from 14 to 18, or a residue formed by elimination of one molecule of water from the group corresponding to formula IIIa or IIIb, $R^4O$ is a residue corresponding to formula IIIa or IIIb, in which x, y, z and M are as defined above, or a residue formed by elimination of one molecule of water from the group corresponding to formula IIIa or IIIb or a residue of an alkanol containing from 1 to 12 carbon atoms, m is the number 2 or 3 and n is a number from 1 to 20.

Preferred surface-active agents are those containing, individually or in admixture, carbonic acid fatty alcohol ester sulfonates corresponding to formula II in which $R^3O$ is a residue corresponding to formula IIIa or IIIb derived from a fatty alcohol containing 18 carbon atoms, $R^4O$ is a residue corresponding to formula IIIa or IIIb derived from a fatty alcohol containing 18 carbon atoms, a linear alkoxy group containing 16 to 18 carbon atoms or an ethoxy group, m is the number 2, n is a number of 0 to 10, x and z are a number of 0 to 14 and y is the number 0, 1 or 2, the sum $x+y+z=14$ and M being as defined above.

Mixtures of surface-active agents of the type herein typically comprise compounds corresponding to formula II in which $R^3O$ is an optionally ethoxylated and hydroxy-, sulfato-substituted oleyloxy radical. The group $R^4O$ may have the same meaning as defined for the group $R^3O$. However, the mixture also contains compounds in which $R^4O$ is the residue of a saturated alkanol containing 1 to 22 carbon atoms, for example an ethoxy group in admixture with cetyl and/or stearyloxy groups. The ethoxy group emanates from diethyl carbonate which was not fully reacted in the preparation of the starting compound corresponding to formula I while the cetyloxy or stearyloxy groups emanate from cetyl and stearyl alcohol present in technical grade oleyl alcohol cuts.

The invention is illustrated by the following Examples.

PREPARATION OF STARTING COMPOUNDS

A. Bisoleyl carbonate

A technical grade oleyl alcohol having the following characteristic data was used: C chain distribution: $C_{14}=0$ to 2%, $C_{16}=2$ to 10%, $C_{18}=87$ to 95%, $C_{20}=0$ to 3%. Iodine value: 90 to 97. OH value: 205 to 215.

268 g (1 mol) of the oleyl alcohol mentioned above and 59 g (0.5 mol) of diethyl carbonate were introduced into a 1-liter round-bottomed flask equipped with a distillation column, followed by the addition of 1 g (corresponding to 0.5 mol-%) of sodium methylate in the form of a 30% methanolic solution. The reaction mixture was heated for 1 hour to 120° C. and then kept at 150° C. for 30 minutes. Ethanol liberated was distilled off. The product was then freed from residues of alcohol for 2 hours at 120° C. in a water jet vacuum and neutralized with acetic acid.

Approximately 320 g of product was obtained in the form of a light yellow, readily mobile liquid having an OH value of 9.5, an acid value of 0.1, an iodine value of 48 and a number average molecular weight of 548.

B. Bis(oleyl-5EO) carbonate 478 g (1 mol) of a commercially available adduct of 5 mol of ethylene oxide with 1 mol of the oleyl alcohol mentioned above were reacted with 59 g (0.5 mol) of diethyl carbonate as described above under A. The title compound was obtained in a yield of approximately 550 g in the form of a light yellow, cloudy liquid having an OH value of 8.5, an acid value of 0.1, an iodine value of 31 and a number average molecular weight of 905.

C. Bis-(oleyl-10EO) carbonate 707 g (1 mol) of a commercially available adduct of 10 mol of ethylene oxide with 1 mol of the technical grade oleyl alcohol described above were reacted with 59 g (0.5 mol) of diethyl carbonate in the same way as described under A. The title compound was obtained in a yield of approximately 760 g in the form of a pale yellow colored, cloudy liquid having an OH value of 7.3, an acid value of 0.1, an iodine value of 20 and a number average molecular weight of 1402.

D. Oleyl cetyl carbonate

A technical grade oleyl/cetyl alcohol mixture having the following characteristic data was used: C chain distribution: $C_{12}=0$ to 2%, $C_{14}=2$ to 7%, $C_{16}=27$ to 35%, $C_{18}=55$ to 75%, $C_{20}=0$ to 2%. Iodine value: 50 to 55. OH value: 210 to 220.

260 g (1 mol) of the technical grade oleyl/cetyl alcohol mixture were reacted with 59 g (0.5 mol) of diethyl carbonate in the same way as described under A. The title compound was obtained in a yield of approximately 318 g in the form of a colorless, solid mass having an OH value of 9.0, an acid value of 0.1, an iodine value of 24 and a number average molecular weight of 548.

E. Oleyl ethyl carbonate 260 g (1 mol) of a technical grade oleyl alcohol were reacted with 118 g (1 mol) of diethyl carbonate in the same way as described under A. The title compound was obtained in a yield of approximately 370 g in the form of a light yellow, clear liquid having an OH value of 8.5, an acid value of 0.1, an iodine value of 76 and a number average molecular weight of 333.

EXAMPLE 1

Bisoleyl carbonate disulfonate 584 g (1 mol) of bisoleyl carbonate were introduced into a 1 liter sulfonation flask equipped with a jacket cooling system and a gas inlet pipe and reacted with 192 g (2.4 mol) of gaseous sulfur trioxide at a temperature of 40° to 45° C.

The sulfur trioxide was driven out by heating from a corresponding quantity of 65% oleum, diluted with nitrogen to a concentration of 5% by volume and introduced into the carbonic acid diester for 65 minutes, during which the temperature of the reaction mixture was kept by cooling below 60° C.

After the sulfonation, the acidic reaction mixture was stirred into a solution of 104 g (2.6 mol) of sodium hydroxide in 500 ml water, hydrolyzed for 4 hours at 95° C. and then adjusted with mineral acid to a pH value of 7.

| Characteristic data of the product: | |
|---|---|
| Anionic surfactant content: | 16.4% (0.0208 mval/g) |
| Unsulfonated fractions: | 6.7% |
| Sulfate (expressed as $Na_2SO_4$): | 1.9% |
| Water (Fischer's method): | 75.0% |
| Klett color value: | 102 |
| Number average molecular weight: | 788 |

Both here and in the following Examples, the anionic surfactant content and the unsulfonated fractions were determined by the DGF Einheitsmethoden (DGF Standard Methods), Stuttgart 1950–1984, H-III-10 and G-III-6b. The Klett color value was determined after bleaching for 30 minutes with 5% by weight hydrogen peroxide solution. The measurement was performed at a concentration of 5% by weight anionic surfactant and at a pH value of 7 using a 1 cm round cell and a blue filter (400 to 465 nm).

EXAMPLE 2

The procedure was as in Example 1 except using 224 g (2.8 mol) of sulfur trioxide corresponding to a ratio of double bond equivalents to sulfur trioxide of 1:1.4. The sulfur trioxide was introduced for 84 minutes. The crude sulfonation product was neutralized with 120 g (3 mol) of sodium hydroxide in water and then adjusted to a pH value of 6.5 to 7.5.

| Characteristic data of the product: | |
|---|---|
| Anionic surfactant content: | 24.1% (0.0306 mval/g) |
| Unsulfonated fractions: | 2.3% |
| Sulfate (expressed as $Na_2SO_4$): | 2.2% |
| Water (Fischer's method): | 71.4% |
| Klett color value: | 286 |
| Number average molecular weight: | 788 |

EXAMPLE 3

Bis(oleyl-5EO) carbonate disulfonate 496 g of the adduct of 5 mol of ethylene oxide with technical grade oleyl alcohol were reacted as in Example 1 with 96 g (1.2 mol) of sulfur trioxide corresponding to a ratio of double bond equivalents to sulfur trioxide of 1:1.4.

EXAMPLE 4

Bis(oleyl-10EO) carbonate disulfonate 701 g (0.5 mol) of bis(oleyl-10EO) carbonate were reacted as in Example 1 with 96 g (1.2 mol) of sulfur trioxide corresponding to a ratio of double bond equivalents to sulfur trioxide of 1:1.4.

Characteristic data of the product:

| | | |
|---|---|---|
| Anionic surfactant content: | 19.0% | (0.0118 mval/g) |
| Unsulfonated fractions: | 7.7% | |
| Sulfate (expressed as Na$_2$SO$_4$): | 1.3% | |
| Water (Fischer's method): | 72.0% | |
| Klett color value: | 41 | |
| Number average molecular weight: | 1606 | |

EXAMPLE 5

Oleyl cetyl carbonate sulfonate 548 g (1 mol) of oleyl cetyl carbonate were reacted as in Example 1 with 96 g (1.2 mol) of sulfur trioxide corresponding to a ratio of double bond equivalents to sulfur trioxide of 1:1.2, followed as described above by neutralization with 56 g NaOH in water.

Characteristic data of the product:

| | | |
|---|---|---|
| Anionic surfactant content: | 9.8% | (0.0150 mval/g) |
| Unsulfonated fractions: | 13.1% | |
| Sulfate (expressed as Na$_2$SO$_4$): | 1.8% | |
| Water (Fischer's method): | 75.3% | |
| Klett color value: | 66 | |
| Average molecular weight: | 650 | |

EXAMPLE 6

Oleyl ethyl carbonate sulfate 333 g (1 mol) of oleyl ethyl carbonate were reacted as described in Example 1 with 96 g (1.2 mol) of sulfur trioxide corresponding to a ratio of double bond equivalents to sulfur trioxide of 1:1.2, followed as described above by neutralization with 56 g NaOH in water.

Characteristic data of the product:

| | | |
|---|---|---|
| Anionic surfactant content: | 19.1% | (0.0439 mval/g) |
| Unsulfonated fractions: | 7.5% | |
| Sulfate (expressed as Na$_2$SO$_4$): | 1.4% | |
| Water (Fischer's method): | 72.0% | |
| Klett color value: | 96 | |
| Average molecular weight: | 435 | |

We claim:

1. A carbonic acid fatty alcohol ester sulfonate prepared by sulfonating a carbonic acid fatty alcohol ester corresponding to formula I $$R^1O-(C_mH_{2m}O)_n-CO-(OC_mH_{2m})_n-OR^2 \qquad (I)$$

in which
- R$^1$O is a radical of a fatty alcohol containing 16 to 22 carbon atoms and at least one olefinic double bond,
- R$^2$O is a radical of a saturated alkanol containing 1 to 22 carbon atoms or a radical of a fatty alcohol containing 16 to 22 carbon atoms and at least one olefinic double bond,
- m is the number 2 or 3 and
- n is a number of 0 to 20, and subsequent neutralizing and hydrolyzing the sulfonation product with base to provide a carbonic acid fatty alcohol ester sulfonate corresponding to formula II $$R^3O-(C_mH_{2m}O)_n-CO-(OC_mH_{2m})_n-OR^4 \qquad (II)$$

in which R$^3$O is a radical corresponding to formula IIIa or IIIb $$CH_3-(CH_2)_x-CH(OH)-(CH_2)_y-CH(SO_3M)-(CH_2)_z-CH_2-O- \qquad (IIIa)$$

or $$CH_3-(CH_2)_x-CH(SO_3M)-(CH_2)_y-CH(OH)-(CH_2)_z-CH_2-O- \qquad (IIIb)$$

in which
- x and z are a number of 0 to 18,
- y is the number 0, 1 or 2 and
- y is the number 0, 1 or 2 and
- M is an alkali metal, ammonium, mono-, di- or trialkyl- or hydroxyalkyl-substituted ammonium ion,
- the sum of x+y+z being a number in the range from 14 to 18, or a radical formed by elimination of one molecule of water from the group corresponding to formula IIIa or IIIb,
- R$^4$O is a residue corresponding to formula IIIa or IIIb in which x, y, z and M are as defined above, or a radical of an alkanol containing from 1 to 12 carbon atoms,
- m is the number 2 or 3 and
- n is a number from 1 to 20.

2. A carbonic acid fatty alcohol ester sulfonate as in claim 1 prepared by sulfonating a carbonic acid fatty alcohol ester corresponding to formula I in which
- R$^1$O is an oleyloxy group,
- R$^2$O is an oleyloxy, cetyloxy, stearyloxy or ethyloxy group,
- m is the number 2 and
- n is a number of 0 to 10.

3. A carbonic acid fatty alcohol ester sulfonate as in claim 1 prepared by sulfonating a carbonic acid fatty alcohol ester corresponding to formula I in which R$^1$O, R$^2$O, m and n are as defined above, with sulfur trioxide and subsequently neutralizing and hydrolyzing the sulfonation product with a base.

4. A carbonic acid fatty alcohol ester sulfonate as in clam 1 wherein said sulfonating is carried out at a ratio of about 0.5 to about 1.8 mol of sulfur trioxide per mol of the olefinic double bonds present in said carbonic acid fatty alcohol ester at a temperature in the range of from about 15° to about 80° C.

5. A carbonic acid fatty alcohol ester sulfonate as in claim 1 wherein said sulfonating is carried out at a ratio of about 1.0 to about 1.3 mol of sulfur trioxide per mol of olefinic double bond present in said carbonic acid fatty alcohol ester.

6. A carbonic acid fatty alcohol ester sulfonate as in claim 1 wherein said neutralizing and hydrolyzing of the sulfonation product with a base is carried out at a pH value of from about 7 to about 12.

7. A carbonic acid fatty alcohol ester sulfonate as in claim 1 wherein the hydrolysis of the neutralized sulfonation product is carried out for about 15 to about 240 minutes at a temperature of at least about 70° C.

8. A surface-active compound of a carbonic acid fatty alcohol ester sulfonate corresponding to formula II $$R^3O-(C_mH_{2m}O)_n-CO-(OC_mH_{2m})_n-OR^4 \quad (II)$$

in which $R^3O$ is a radical corresponding to formula IIIa or IIIb $$CH_3-(CH_2)_x-CH(OH)-(CH_2)_y-CH(SO_3M)-(CH_2)_z-CH_2-O- \quad (IIIa)$$

or $$CH_3-(CH_2)_x-CH(SO_3M)-(CH_2)_y-CH(OH)-(CH_2)_z-CH_2-O- \quad (IIIb)$$

in which
x and z are a number of 0 to 18,
y is the number 0, 1 or 2 and
M is an alkali metal, ammonium, mono-, di- or trialkyl- or hydroxyalkyl-substituted ammonium ion,
the sum of x+y+z being a number from 14 to 18,
or a radical formed by elimination of one molecule of water from the group corresponding to formula IIIa or IIIb,
$R^4O$ is a residue corresponding to formula IIIa or IIIb in which x, y, z and M are as defined above, or a radical of an alkanol containing from 1 to 12 carbon atoms,
m is the number 2 or 3 and
n is a number from 1 to 20.

9. A surface-active compound as in claim 8 wherein $R^3O$ is a radical corresponding to formula IIIa or IIIb derived from a $C_{18}$ fatty alcohol,
$R^4O$ is a radical corresponding to formula IIIa or IIIb derived from a $C_{18}$ fatty alcohol, a linear $C_{16-18}$ alkoxy group, or an ethoxy group,
m is the number 2,
n is a number of 0 to 10,
x and z are a number of 0 to 14,
y is the number 0, 1 or 2, and
the sum x+y+z is equal to 14.

* * * * *